(12) United States Patent
Tobe et al.

(10) Patent No.: US 6,953,871 B2
(45) Date of Patent: Oct. 11, 2005

(54) PROCESSES FOR PRODUCING POLY-ETHYNYL-SUBSTITUTED AROMATIC COMPOUND

(75) Inventors: Yoshito Tobe, Ashiya (JP); Motohiro Sonoda, Mino (JP)

(73) Assignee: Japan Science and Technology Corporation, Saitama (JP)

( * ) Notice: Subject to any disclaimer, the term of this patent is extended or adjusted under 35 U.S.C. 154(b) by 208 days.

(21) Appl. No.: 10/471,369

(22) PCT Filed: Dec. 27, 2001

(86) PCT No.: PCT/JP01/11607

§ 371 (c)(1),
(2), (4) Date: Sep. 11, 2003

(87) PCT Pub. No.: WO02/072589

PCT Pub. Date: Sep. 19, 2002

(65) Prior Publication Data

US 2004/0111000 A1 Jun. 10, 2004

(30) Foreign Application Priority Data

Mar. 13, 2001 (JP) ........................................ 2001-069769

(51) Int. Cl.$^7$ ................................................. C07C 1/26
(52) U.S. Cl. ..................................... 585/469; 585/314
(58) Field of Search .................................. 585/469, 319

(56) References Cited

U.S. PATENT DOCUMENTS 5,498,367 A    3/1996   Buchecker et al.

FOREIGN PATENT DOCUMENTS

EP           675188 A1   10/1995

OTHER PUBLICATIONS

Bowles et al., Organic Letters, vol. 2, No. 1, pp. 85–87 (2000).
Diercks et al., Agnew. Chem. Int. Ed. Engl., 25 (1986) No. 3, 268–269.
Anthony et al., Tetrahedron Letters, vol. 38, No. 20, pp. 3499–3502, 1997.
Tobe et al., J. Org. Chem. 1997, 62, 3430–3431.
Tovar et al., J. Org. Chem. 1997, 62, 3432–3433.
Bowles et al., Tetrahedron 57 (2001) 3753–3760.
Sonoda et al., Organic Letters 2001, vol. 3, No. 15, 2419–2421.
Hirao, T. et al., J. Org. Chem., 2000, vol. 65, No. 5, pp. 1511–1515, Particularly, p. 1513; Table 3, entry 3, 4, 11.
Negishi E. et al., J. Chem. Soc., Chem Commun., 1987, No. 6, pp. 477–478, Particularly p. 477, lower right column; reaction drawing.

*Primary Examiner*—Thuan D Dang
(74) *Attorney, Agent, or Firm*—Birch, Steward, Kolasch & Birch, LLP

(57) ABSTRACT

A process for preparing a poly-ethynyl-substituted aromatic compound characterized by reacting a halogenated benzene with an ethynylzinc halide; a process for preparing a poly-ethynyl-substituted aromatic compound characterized by using a halogenated benzene having at least two kinds of halogen atoms as a halogenated benzene, and (A) reacting one kind of the halogen atoms existing in the halogenated benzene with an ethynyl group-containing compound; and (B) reacting the other kind of halogen atoms remaining in the formed compound with an ethynylzinc halide. The poly-ethynyl-substituted aromatic compound is used as liquid crystals, nonlinear optical materials, electroconductive materials and the like

3 Claims, No Drawings

PROCESSES FOR PRODUCING POLY-ETHYNYL-SUBSTITUTED AROMATIC COMPOUND

This application is the national phase under 35 U.S.C. § 371 of PCT International Application No. PCT/JP01/11607 which has an International filing date of Dec. 27, 2001, which designated the United States of America.

TECHNICAL FIELD

The present invention relates to a process for preparing a poly-ethynyl-substituted aromatic compound. More specifically, the present invention relates to a process for preparing a poly-ethynyl-substituted aromatic compound which can be suitably used as liquid crystals, nonlinear optical materials, electroconductive materials and the like.

BACKGROUND ART

Poly-ethynyl-substituted aromatic compounds in which a π (pi) electron system is bonded to the benzene ring with a triple bond have been considered to be applied as liquid crystals, nonlinear optical materials and electroconductive materials, and are a group of compounds useful as synthetic blocks for dendrimer type π conjugated systems and carbon-rich materials of optical and photochemical interests.

Although these compounds have been usually prepared by a catalytic coupling reaction of a halogenated benzene with acetylene (generally referred to as the Sonogashira reaction) [R. Diercks, J. C. Armstrong, R. Boese, K. P. C. Vollhardt, Angew. Chem., Int. Ed. Engl., 25, 268(1986)], the efficiency of the coupling reaction is not high except for the compounds having phenyl group at its acetylene terminal. For instance, hexakis[(trimethylsilyl)ethynyl]benzene is prepared by coupling of hexabromobenzene with (trimethylsilyl)acetylene, but its yield is at most 30%. Also, there has hitherto been no general and efficient process for preparing a poly-ethynyl-substituted aromatic compound having a different substituent at its acetylene terminal at all, nevertheless there are of increasing interests from the viewpoints of the above applications [conventional processes: J. E. Anthony, S. I. Khan, Y. Rubin, Tetrahedron Lett., 38, 3499 (1997); Y. Tobe, K. Kubota, K. Naemura, J. Org. Chem., 62, 3430 (1997); J. D. Tovar, N. Jux, T. Jarrosson, S. I. Khan, Y. Rubin, ibid, 62, 3432 (1997)].

In addition, in the conventional processes for preparing poly-ethynyl-substituted aromatic compounds, substitution patterns for poly-ethynyl-substituted aromatic compounds having different ethynyl-terminal substituents could not have been controlled.

DISCLOSURE OF INVENTION

The present invention has been accomplished in view of the above prior art, and an object of the present invention is to provide a process for efficiently preparing a poly-ethynyl-substituted aromatic compound.

A further object of the present invention is to provide a process for preparing a poly-ethynyl-substituted aromatic compound having a specific substituent at a specified position.

The gist of the present invention relates to:
(1) a process for preparing a poly-ethynyl-substituted aromatic compound characterized by reacting a halogenated benzene with an ethynylzinc halide; and
(2) a process for preparing a poly-ethynyl-substituted aromatic compound characterized by using a halogenated benzene having at least two kinds of halogen atoms as a halogenated benzene, and
(A) reacting one kind of the halogen atoms existing in the halogenated benzene with an ethynyl group-containing compound; and
(B) reacting the other kind of halogen atoms remaining in the formed compound with an ethynylzinc halide.

BEST MODE FOR CARRYING OUT THE INVENTION

The halogenated benzene used in the present invention includes one in which all of hydrogen atoms existing in the benzene ring are substituted with a halogen atom; one in which hydrogen atoms existing in the benzene ring are substituted with a halogen atom and other substituent; and the like. It is desired that the number of the substituting halogen atoms of the benzene ring is usually 2 to 8, preferably 4 to 6.

Concrete examples of the halogenated benzene in which all of hydrogen atoms existing in the benzene ring are substituted with a halogen atom include those in which all of the substituting halogen atoms are the same kind, such as hexabromobenzene, hexachlorobenzene and hexaiodobenzene; those in which the hydrogen atoms are substituted with at least two kinds of halogen atoms, such as 1-chloro-2,3,4,5,6-pentaiodobenzene, 1,2-dichloro-3,4,5,6-tetraiodobenzene, 1,3-dichloro-2,4,5,6-tetraiodobenzene, 1,4-dichloro-2,3,5,6-tetraiodobenzene, 1,2,3-trichloro-4,5,6-triiodobenzene, 1,2,4-trichloro-3,5,6-triiodobenzene, 1,3,5-trichloro-2,4,6-triiodobenzene, 1,3,5-tribromo-2,4,6-trichlorobenzene, 1,3,5-tribromo-2,4,6-triiodobenzene, 1,2,3,4-tetrachloro-5,6-diiodobenzene, 1,2,3,5-tetrachloro-4,6-diiodobenzene, 1,2,4,5-tetrachloro-3,6-diiodobenzene and 1,2,3,4,5-pentachloro-6-iodobenzene; and the like. However, the present invention is not limited to those exemplified ones. Among them, hexabromobenzene, 1,3,5-trichloro-2,4,6-triiodobenzene and the like can be suitably used in the present invention.

In the halogenated benzene in which hydrogen atoms existing in the benzene ring are substituted with a halogen atom and other substituent, the other substituent includes, for instance, a (trialkylsilyl)ethynyl group of which alkyl group has 1 to 4 carbon atoms and the like. Among them, (trimethylsilyl)ethynyl group is preferable.

Concrete examples of the halogenated benzene in which hydrogen atoms existing in the benzene ring are substituted with a halogen atom and other substituent include 1,3,5-trichloro-2,4,6-tris[(trimethylsilyl)ethynyl]benzene, 1,3,5-tribromo-2,4,6-tris[(trimethylsilyl)ethynyl]benzene, 1,3,5-triiodo-2,4,6-tris[(trimethylsilyl)ethynyl]benzene, and the like. However, the present invention is not limited to those exemplified ones. Among them, 1,3,5-trichloro-2,4,6-tris[(trimethylsilyl)ethynyl]benzene and the like can be suitably used in the present invention.

Representative examples of the ethynylzinc halide include ethynylzinc chloride and ethynylzinc bromide. The kind of the ethynylzinc halide cannot be absolutely determined because it differs depending upon the kind of an objective compound. For instance, when a poly-ethynyl-substituted aromatic compound having (trimethylsilyl)ethynyl group is prepared, (trimethylsilyl)ethynylzinc chloride can be used as an ethynylzinc halide, and when a poly-ethynyl-substituted aromatic compound having phenylethynyl group is prepared, phenylethynylzinc chloride can be used as an ethynylzinc halide.

The ethynylzinc halide can be readily prepared by, for instance, reacting an ethynyl group-containing compound such as (trimethylsilyl)acetylene or phenylacetylene with zinc chloride or zinc bromide in an organic solvent such as tetrahydrofuran in the presence of a base such as n-butyllithium.

In the reaction of the halogenated benzene with the ethynylzinc halide, the amount of the ethynylzinc halide differs depending upon the kind of the halogenated benzene. It is usually necessary that the amount of the ethynylzinc halide is equivalent to the amount of the halogen atoms in order to react all of the halogen atoms existing in the halogenated benzene with the ethynylzinc halide. It is preferable that the amount is excess, for instance, about 1.2 to about 8 equivalents of the halogen atoms from the viewpoint of efficiently reacting the halogen atoms with the ethynylzinc halide.

The reaction of the halogenated benzene with the ethynylzinc halide can be carried out, for instance, in an organic solvent such as tetrahydrofuran or toluene. The amount of the organic solvent is not limited to specified ones, and is usually about 100 to about 20000 parts by weight based on 100 parts by weight of the halogenated benzene. It is preferable that the reaction is carried out by previously dissolving the halogenated benzene in an organic solvent, and previously suspending the ethynylzinc halide in the organic solvent, and thereafter mixing them.

In the reaction, it is preferable to use a catalyst from the viewpoint of accelerating the reaction. The catalyst includes, for instance, tetrakis(triphenylphosphine)palladium [hereinafter referred to as $Pd(PPh_3)_4$], bis(triphenylphosphine)palladium(II) chloride, bis(benzonitrile)palladium(II) chloride, tris(dibenzylideneacetone)dipalladium, palladium(II) chloride, palladium(II) acetate and the like. It is preferable that the amount of the catalyst is about 0.01 to about 0.3 mol per one mol of the halogenated benzene in consideration of reaction rate and removal efficiency of the catalyst after the reaction.

It is preferable that the atmosphere during the reaction is, for instance, an inert gas atmosphere such as nitrogen gas or argon gas.

More specifically, the reaction of the halogenated benzene with the ethynylzinc halide can be carried out by firstly dissolving a halogenated benzene in an organic solvent, and adding a suspension of an ethynylzinc halide in an organic solvent to the solution.

The reaction temperature may be 50° C. to a reflux temperature from the viewpoint of accelerating the reaction.

The reaction time is usually 10 to 100 hours or so. The termination of the reaction can be confirmed by, for instance, high-performance liquid chromatography using a reversed phase column. When the halogenated benzene remains in the reaction mixture, a catalyst and an ethynylzinc halide may be further added thereto to progress the reaction as occasion demands.

After the termination of the reaction, an extraction solvent such as diethyl ether is added to the reaction mixture, the mixture is washed with hydrochloric acid, brine or the like, and water is removed from the separated organic layer with a desiccant such as anhydrous magnesium sulfate. Thereafter, the organic solvent is distilled off under reduced pressure, and the resulting solid is isolated by, for instance, silica gel column chromatography or the like, whereby a poly-ethynyl-substituted aromatic compound, which is an objective compound, can be obtained. The resulting poly-ethynyl-substituted aromatic compound may be purified by, for instance, recycling preparative liquid chromatography using a gel permeation column or the like, as occasion demands.

As explained above, according to the process for preparing a poly-ethynyl-substituted aromatic compound of the present invention, there can be efficiently substituted, for instance, an ethynylzinc halide derived from an ethynyl group-containing compound such as (trimethylsilyl) acetylene, with a halogen atom of the halogenated benzene. In addition, when the halogen atom of the halogenated benzene is substituted with (trimethylsilyl)ethynyl group, a benzene having (trimethylsilyl)ethynyl group is obtained, and its terminal trimethylsilyl group can be further substituted with $\pi$ (pi) electron system. Therefore, according to the process of the present invention, various kinds of 6-substituted-ethynylbenzene can be relatively conveniently prepared.

In addition, according to the process for preparing a poly-ethynyl-substituted aromatic compound of the present invention, a poly-ethynyl-substituted aromatic compound having a specific substituent at a specified position can be obtained by properly selecting the difference in the reactivity of the halogen atom of the halogenated benzene to a coupling reaction between a halogenated benzene having at least two kinds of halogen atoms and an ethynyl group-containing compound or an ethynylzinc halide and by properly selecting the reaction conditions.

Specifically, the poly-ethynyl-substituted aromatic compound having a specific substituent at a specified position can be obtained by using a halogenated benzene having at least two kinds of halogen atoms as a halogenated benzene, and (A) reacting one kind of the halogen atoms existing in the above halogenated benzene with an ethynyl group-containing compound; and (B) reacting the other kind of halogen atoms remaining in the formed compound with an ethynylzinc halide.

In the step (A), one kind of a halogen atom existing in the halogenated benzene is reacted with the ethynyl group-containing compound. Also, in the step (B), the other kind of the halogen atoms remaining in the formed compound is reacted with the ethynylzinc halide in accordance with the same method as described above.

The ethynyl group-containing compound used in the step (A) may be a compound having an ethynyl group capable of reacting with a halogen atom existing in the halogenated benzene. Usually, the kind of the ethynyl group-containing compound may be properly selected in accordance with the kind of an objective compound. Concrete examples of the ethynyl group-containing compound include (trimethylsilyl) acetylene, phenylacetylene and the like.

The amount of the ethynyl group-containing compound used in the step (A) cannot be absolutely determined because the amount differs depending upon the number of the halogen atoms existing in the halogenated benzene. It is necessary that the amount of the ethynyl group-containing compound is usually equivalent to the amount of the halogen atom in order to react all of the one kind of the halogen atoms existing in the halogenated benzene with the ethynyl group-containing compound. It is preferable that the amount of the ethynyl group-containing compound is excess, for instance about 1.2 to about 2 equivalents of the halogen atoms from the viewpoint of efficiently reacting the halogen atoms with the ethynyl group-containing compound.

The reaction of one kind of a halogen atom existing in the halogenated benzene with the ethynyl group-containing compound can be carried out, for instance, in an organic solvent such as tetrahydrofuran. The amount of the organic solvent is not limited to specified ones, and is usually about 1000 to about 10000 parts by weight based on 100 parts by weight of the halogenated benzene.

In the reaction, it is preferable to use a base from the viewpoint of accelerating the reaction. The base includes, for instance, diisopropylamine, triethylamine, diethylamine, n-butylamine, pyridine, piperidine, pentamethylpiperidine and the like. It is preferable that the amount of the base is about 1.2 to about 10 mol per one mol of the halogenated benzene, in consideration of reaction rate and removal efficiency of the base after the reaction.

In the reaction, it is preferable that two kinds of the catalysts are used together from the viewpoint of accelerating the reaction.

One of the two kinds of the catalysts used in the reaction includes, for instance, tetrakis(triphenylphosphine) palladium [hereinafter referred to as Pd(PPh$_3$)$_4$], bis(triphenylphosphine)palladium(II) chloride, bis(benzonitrile)palladium(II) chloride, tris(dibenzylideneacetone)dipalladium, palladium(II) chloride, palladium(II) acetate, and the like. It is preferable that the amount of the catalyst is about 0.01 to about 0.3 mol per one mol of the halogenated benzene in consideration of reaction rate and removal efficiency of the catalyst after the reaction.

The other catalyst used together with the above catalyst includes, for instance, copper iodide [hereinafter referred to as CuI], copper bromide, copper chloride and the like. Among them, CuI and the like can be suitably used in the present invention. It is preferable that the amount of this catalyst is about 0.01 to about 3 mol per one mol of the halogenated benzene in consideration of reaction rate and removal efficiency of the catalyst after the reaction.

It is preferable that the atmosphere during the reaction is, for instance, an inert gas atmosphere such as nitrogen gas or argon gas.

More specifically, the reaction of one kind of a halogen atom existing in the halogenated benzene with the ethynyl group-containing compound can be carried out by firstly mixing a halogenated benzene, an organic solvent, a catalyst and a base, and then adding an ethynyl group-containing compound to the resulting mixture.

The reaction temperature may be 60° C. to a reflux temperature from the viewpoint of accelerating the reaction.

The reaction time is usually 10 to 60 hours or so. The termination of the reaction can be confirmed by, for instance, high-performance liquid chromatography using a reversed phase column, or the like.

After the termination of the reaction, an extraction solvent such as diethyl ether is added to the reaction mixture, the mixture is washed with hydrochloric acid, aqueous sodium hydrogencarbonate, brine or the like, and water is removed from the separated organic layer with a desiccant such as anhydrous magnesium sulfate. Thereafter, the organic solvent is distilled off under reduced pressure, and the resulting solid is isolated by, for instance, silica gel column chromatography or the like, whereby a poly-ethynyl-substituted aromatic compound, which is an objective compound, can be obtained. The resulting poly-ethynyl-substituted aromatic compound may be purified by, for instance, recycling preparative liquid chromatography using a gel permeation column, or the like, as occasion demands.

As one embodiment of the above-mentioned process, for instance, when 1,3,5-tris[(trimethylsilyl)ethynyl]-2,4,6-tris(phenylethynyl)benzene is an objective compound, 1,3,5-trichloro-2,4,6-triiodobenzene which can be readily prepared from 1,3,5-trichlorobenzene is used as a starting material (halogenated benzene), and reacted with (trimethylsilyl)acetylene as an ethynyl group-containing compound. As a result, only the iodine atoms having high reactivity are firstly substituted with (trimethylsilyl) acetylene according to Sonogashira reaction, whereby 1,3,5-trichloro-2,4,6-tris[(trimethylsilyl)ethynyl]benzene in which the chlorine atoms remain intact can be obtained in a high yield.

Next, the formed 1,3,5-trichloro-2,4,6-tris[(trimethylsilyl)ethynyl]benzene is reacted with phenylethynylzinc chloride as an ethynylzinc halide. As a result, the chlorine atoms are substituted with phenylacetylene, and an objective 1,3,5-tris[(trimethylsilyl)ethynyl]-2,4,6-tris(phenylethynyl)benzene can be obtained.

As another embodiment, for instance, when 1,3,5-trichloro-2,4,6-triiodobenzene is reacted with phenylacetylene and (trimethylsilyl)ethynylzinc chloride as the ethynyl group-containing compound in order, in place of reacting (trimethylsilyl)acetylene and phenylethynylzinc chloride in order, all of the iodine atoms and one chlorine atom of 1,3,5-trichloro-2,4,6-triiodobenzene are reacted with phenylacetylene in the reaction of 1,3,5-trichloro-2,4,6-triiodobenzene with phenylacetylene under the same conditions as in the step (A), to give 1,3-dichloro-2,4,5,6-tetrakis(phenylethyl)benzene. In the step (B), when this compound is reacted with (trimethylsilyl)ethynylzinc chloride, 1,3-bis[(trimethylsilyl)ethynyl]-2,4,5,6-tetrakis(phenylethynyl)benzene can be obtained.

As described above, according to the process of the present invention, the poly-ethynyl-substituted aromatic compound having a specific ethynyl substituent at a specified position can be efficiently obtained, for instance, by properly controlling the reactivity of chlorine atoms and iodine atoms and reaction conditions.

EXAMPLES

Example 1

Preparation of Hexakis[(trimethylsilyl)ethynyl]benzene (1) Preparation of [(Trimethylsilyl)ethynyl]zinc Reagent A rotator was placed in a 50 mL three neck flask, and the flask was equipped with a condenser and a blowing tube. The whole of the apparatus was dried, and thereafter allowed to cool to room temperature under a nitrogen atmosphere.

The flask was charged with 986 mg (10.0 mmol) of (trimethylsilyl)acetylene and 4 mL of tetrahydrofuran, and the mixture was cooled to −78° C. in a cooling bath with ethanol and dry ice. Thereafter, 6.3 mL (9.7 mmol) of a 1.56 mol/L hexane solution of n-butyllithium was slowly added over a period of 30 minutes. After stirring the mixture at −78° C. for 1 hour, a suspension of 1.43 g (10.5 mmol) of zinc chloride in 6 mL of tetrahydrofuran was added thereto. The mixture was stirred at −78° C. for additional 1 hour, and thereafter the cooling bath was removed, and the mixture was allowed to stand upto room temperature. The solution was used as [(trimethylsilyl)ethynyl]zinc reagent [(CH$_3$)$_3$Si—C≡C—ZnCl].

(2) Preparation of Hexakis[(trimethylsilyl)ethynyl]benzene

A rotator was placed in a 30 mL two neck flask, and the flask was equipped with a condenser and a blowing tube. The whole of the apparatus was dried, and thereafter allowed to cool to room temperature under a nitrogen atmosphere.

The flask was charged with 550 mg (1.0 mmol) of hexabromobenzene, 210 mg (0.19 mmol) of Pd(PPh$_3$)$_4$ and 7 mL of toluene, and the mixture was stirred at room temperature. Subsequently, the previously prepared suspension of 10 mmol of the [(trimethylsilyl)ethynyl]zinc reagent in 10 mL of tetrahydrofuran was added thereto. The flask was immersed in an oil bath at 80° C., and the contents were reacted for 67 hours. The reaction progress was monitored by high-performance liquid chromatography using a reversed phase column.

After the termination of the reaction, 50 mL of diethyl ether was added to the resulting reaction mixture, and the mixture was washed with 50 mL of a 0.5 N hydrochloric acid and 100 mL of saturated brine. Anhydrous magnesium sulfate was added as a desiccant to a separated organic layer, and the organic layer was dried for 1 hour. After the desiccant was removed by filtration, the solvent was distilled off under reduced pressure, to give 1.20 g of a brown sticky solid. The product was isolated and purified by silica gel column chromatography, to give 418 mg of hexakis[(trimethylsilyl)ethynyl]benzene, a pale yellow solid in 64% isolated yield.

In addition, 54 mg of pentakis[(trimethylsilyl)ethynyl]benzene, a pale yellow solid, was obtained as a by-product, in 9% isolated yield.

Example 2

Preparation of 1,3,5-Tris[(trimethylsilyl)ethynyl]-2,4,6-tris(phenylethynyl)benzene (1) Preparation of 1,3,5-Trichloro-2,4,6-tris[(trimethylsilyl)ethynyl]benzene A rotator was placed in a 300 mL three neck flask, and the flask was equipped with a condenser and a blowing tube. The whole of the apparatus was dried, and thereafter allowed to cool to room temperature under a nitrogen atmosphere.

The flask was charged with 11.2 g (20.0 mmol) of 1,3,5-trichloro-2,4,6-triiodobenzene, 2.08 g (1.80 mmol) of $Pd(PPh_3)_4$ and 686 mg (3.60 mmol) of CuI, and thereafter the inside of the flask was replaced with argon. Subsequently, 10.1 mL of diisopropylamine, 80 mL of tetrahydrofuran and 8.84 g (90.0 mmol) of (trimethylsilyl)acetylene were added thereto.

The flask was immersed in an oil bath at 75° C., and the contents were reacted for 30 hours. The reaction progress was monitored by a high-performance liquid chromatography using a reversed phase column. After the termination of the reaction, the reaction mixture was filtered using silica gel column chromatography. To this filtrate were added 100 mL of diethyl ether and 100 mL of water, and a 1 N hydrochloric acid until the aqueous layer became acidic. After the extraction with ether, the organic layer was washed with 50 mL of an aqueous saturated sodium hydrogencarbonate solution and 50 mL of saturated brine. Anhydrous magnesium sulfate was added to a separated organic layer as a desiccant, and the organic layer was dried for 1 hour. The desiccant was removed by filtration, and the solvents were distilled off under reduced pressure.

The resulting residue was separated by silica gel column chromatography, and further recrystallized (solvent for recrystallization: hexane), to give 1,3,5-trichloro-2,4,6-tris[(trimethylsilyl)ethynyl]benzene as a white solid. Further, the mother liquor of the recrystallization was concentrated and purified by recycling preparative liquid chromatography using a gel permeation column, to give 5.79 g of 1,3,5-trichloro-2,4,6-tris[(trimethylsilyl)ethynyl]benzene in 62% isolated yield.

(2) Preparation of (Phenylethynyl)zinc Reagent

A rotator was placed in a 30 mL three neck flask, and the flask was equipped with a condenser and a blowing tube. The whole of the apparatus was dried, and thereafter allowed to cool to room temperature under a nitrogen atmosphere.

The flask was charged with 120 mg (1.1 mmol) of phenylacetylene and 4 mL of tetrahydrofuran, and the flask was cooled to −78° C. in a cooling bath with ethanol and dry ice. Thereafter, 0.65 mL (1.0 mmol) of a 1.56 mol/L hexane solution of n-butyllithium was slowly added over a period of 20 minutes. After stirring the mixture at −78° C. for 30 minutes, a suspension of 140 mg (1.0 mmol) of zinc chloride in 1 mL of tetrahydrofuran was added thereto. The mixture was stirred at −78° C. for additional 1 hour, thereafter the cooling bath was removed, and the mixture was allowed to stand upto room temperature. The resulting solution was used as (phenylethynyl)zinc reagent [(Ph—C≡C—ZnCl].

(3) Preparation of 1,3,5-Tris[(trimethylsilyl)ethynyl]-2,4,6-tris(phenylethynyl)benzene A rotator was placed in a 30 mL two neck flask, and the flask was equipped with a condenser and a blowing tube. The whole of the apparatus was dried, and thereafter allowed to cool to room temperature under a nitrogen atmosphere.

The flask was charged with 47 mg (0.1 mmol) of 1,3,5-trichloro-2,4,6-tris[(trimethylsilyl)ethynyl]benzene and 19 mg (0.017 mmol) of $Pd(PPh_3)_4$, and the previously prepared suspension of 1.0 mmol of the (phenylethynyl)zinc reagent in 6 mL of tetrahydrofuran was added thereto. The flask was immersed in an oil bath at 90° C., and the mixture was refluxed. The reaction progress was monitored by high-performance liquid chromatography using a reversed phase column.

After 24 hours passed, a solution of 1.5 mL tetrahydrofuran containing 12 mg (0.010 mmol) of $Pd(PPh_3)_4$ was added thereto. After 48 hours passed from the beginning of the reaction, a fresh suspension of 1.0 mmol of a (phenylethynyl)zinc reagent in 6 mL of tetrahydrofuran was added thereto. After 90 hours passed from the beginning of the reaction, the reaction was stopped. To the reaction mixture was added 50 mL of diethyl ether, and the mixture was washed with 100 mL of a 0.5 N hydrochloric acid and saturated brine. Anhydrous magnesium sulfate was added as a desiccant to a separated organic layer, and the organic layer was dried for 1 hour. After the desiccant was removed by filtration, the solvent was distilled off under reduced pressure, to give 248 mg of a brown sticky solid. The product was separated by silica gel column chromatography, and further purified by recycling preparative liquid chromatography using a gel permeation column, to give 46 mg of 1,3,5-tris[(trimethylsilyl)ethynyl]-2,4,6-tris(phenylethynyl)benzene, a pale yellow solid, in 69% isolated yield.

Example 3

Preparation of 1,3-Bis[(trimethylsilyl)ethynyl]-2,4,5,6-tetrakis(phenylethynyl)benzene (1) Preparation of 1,3-Dichloro-2,4,5,6-tetrakis(phenylethynyl)benzene A rotator was placed in a 50 mL two neck flask, and the flask was equipped with a condenser and a blowing tube. The whole of the apparatus was dried, and thereafter allowed to cool to room temperature under a nitrogen atmosphere.

The flask was charged with 560 mg (1.0 mmol) of 1,3,5-trichloro-2,4,6-triiodobenzene, 120 mg (0.11 mmol) of $Pd(PPh_3)_4$ and 22 mg (0.12 mmol) of copper iodide (CuI), and the inside of the flask was replaced with argon. Subsequently, 0.75 mL of diisopropylamine, 10 mL of tetrahydrofuran and 560 mg (1.0 mmol) of phenylacetylene were added thereto. The flask was immersed in an oil bath at 75° C., and the contents were reacted for 52 hours. The reaction progress was monitored by high-performance liquid chromatography using a reversed phase column.

After the termination of the reaction, 50 mL of diethyl ether was added to the resulting reaction mixture, and the mixture was washed with 50 mL of a 0.5 N hydrochloric acid, 50 mL of an aqueous saturated sodium hydrogencarbonate and 100 mL of saturated brine. Anhydrous magnesium sulfate was added as a desiccant to a separated organic layer, and the organic layer was dried for 1 hour. After the desiccant was removed by using a short column packed with silica gel, the solvents were distilled off under reduced pressure, to give 358 mg of a brown sticky solid. The product was separated by silica gel column chromatography, and further purified by recycling preparative liquid chromatography using a gel permeation column, to give 182 mg of 1,3-dichloro-2,4,5,6-tetrakis(phenylethynyl)benzene, a pale yellow solid, in 33% isolated yield.

(2) Preparation of 1,3-Bis[(trimethylsilyl)ethynyl]-2,4,5,6-tetrakis(phenylethynyl)benzene A rotator was placed in a 50 mL three neck flask, and the flask was equipped with a condenser and a blowing tube. The whole of the apparatus was dried, and thereafter allowed to cool to room temperature under a nitrogen atmosphere.

The flask was charged with 98 mg (1.0 mmol) of (trimethylsilyl)acetylene and 4 mL of tetrahydrofuran, and the flask was cooled to −78° C. in a cooling bath with ethanol and dry ice. To the flask was slowly added 0.65 mL (1.0 mmol) of a 1.56 mol/L hexane solution of n-butyllithium over a period of 30 minutes. After stirring the mixture at −78° C. for 1 hour, a suspension of 140 mg (1.0 mmol) of zinc chloride in 1 mL of tetrahydrofuran was added thereto. The mixture was stirred at −78° C. for additional 1 hour, thereafter the cooling bath was removed, and the mixture was allowed to stand upto room temperature. The resulting solution was used as [(trimethylsilyl)ethynyl]zinc reagent [$(CH_3)_3Si-C\equiv C-ZnCl$].

A rotator was placed in a 30 mL two neck flask, and the flask was equipped with a condenser and a blowing tube. The whole of the apparatus was dried, and thereafter allowed to cool to room temperature under a nitrogen atmosphere.

The flask was charged with 40 mg (0.07 mmol) of 1,3-dichloro-2,4,5,6-tetrakis(phenylethynyl)benzene and 24 mg (0.020 mmol) of $Pd(PPh_3)_4$, and the mixture was stirred at room temperature. Subsequently, a previously prepared suspension of 10 mmol of [(trimethylsilyl)ethynyl]zinc reagent in 5 mL of tetrahydrofuran was added thereto. The flask was immersed in an oil bath at 90° C., and the contents were reacted for 30 hours. The reaction progress was monitored by high-performance liquid chromatography using a reversed phase column.

After the termination of the reaction, 50 mL of diethyl ether was added to the resulting reaction mixture, and the mixture was washed with 50 mL of a 0.5 N hydrochloric acid and 100 mL of saturated brine. Anhydrous magnesium sulfate was added as a desiccant to a separated organic layer, and the organic layer was dried for 1 hour. After the desiccant was removed by filtration, the solvents were distilled off under reduced pressure, to give 96 mg of a brown sticky solid. The product was isolated and purified by silica gel column chromatography, to give 25 mg of 1,3-bis[(trimethylsilyl)ethynyl]-2,4,5,6-tetrakis(phenylethynyl) benzene, a pale yellow solid, in 51% isolated yield.

Industrial Applicability

The poly-ethynyl-substituted aromatic compound obtained according to the process of the present invention can be suitably used as liquid crystals, nonlinear optical materials, electroconductive materials and the like.

What is claimed is:

1. A process for preparing a poly-ethynyl-substituted aromatic compound characterized by using a halogenated benzene having at least two kinds of halogen atoms as a halogenated benzene, and (A) reacting one kind of the halogen atoms existing in said halogenated benzene with an ethynyl group-containing compound; and (B) reacting the other kind of halogen atoms remaining in the formed compound with an ethynylzinc halide.

2. A process for preparing a poly-ethynyl-substituted aromatic compound characterized by using 1,3,5-trichloro-2,4,6-triiodobenzene as a halogenated benzene, and (A) reacting 1,3,5-trichloro-2,4,6-triiodobenzene with (trimethylsilyl)acetylene as an ethynyl group-containing compound; and (B) reacting the formed 1,3,5-trichloro-2,4,6-tris[(trimethylsilyl)ethynyl]benzene with phenylethynylzinc chloride as an ethynylzinc halide.

3. A process for preparing a poly-ethynyl-substituted aromatic compound characterized by using 1,3,5-trichloro-2,4,6-triiodobenzene as a halogenated benzene, and (A) reacting 1,3,5-trichloro-2,4,6-triiodobenzene with phenylacetylene as an ethynyl group-containing compound; and (B) reacting the formed 1,3-dichloro-2,4,5,6-tetrakis(phenylethynyl)benzene, with (trimethylsilyl)ethynylzinc chloride as an ethynylzinc halide.

* * * * *